US006977985B2

(12) United States Patent
Bohn et al.

(10) Patent No.: US 6,977,985 B2
(45) Date of Patent: Dec. 20, 2005

(54) X-RAY LAMINOGRAPHY SYSTEM HAVING A PITCH, ROLL AND Z-MOTION POSITIONING SYSTEM

(75) Inventors: David D Bohn, Ft Collins, CO (US); Donald R Nohavec, Fort Collins, CO (US); Barry Eppler, Loveland, CO (US)

(73) Assignee: Agilent Technologies, Inc., Palo Alto, CA (US)

( * ) Notice: Subject to any disclaimer, the term of this patent is extended or adjusted under 35 U.S.C. 154(b) by 171 days.

(21) Appl. No.: 10/321,255

(22) Filed: Dec. 17, 2002

(65) Prior Publication Data

US 2004/0114713 A1     Jun. 17, 2004

(51) Int. Cl.[7] .............................................. A61B 6/04
(52) U.S. Cl. ........................... 378/27; 378/21; 378/209
(58) Field of Search ...................... 378/20, 21, 23–27, 378/68, 177, 179, 208, 209, 65, 205, 206

(56) References Cited

U.S. PATENT DOCUMENTS

| | | | | |
|---|---|---|---|---|
| 3,868,103 A | * | 2/1975 | Pageot et al. ................... | 5/614 |
| 4,674,107 A | * | 6/1987 | Urban et al. ................... | 378/98 |
| 4,941,164 A | * | 7/1990 | Schuller et al. ............. | 378/205 |
| 4,991,579 A | * | 2/1991 | Allen .......................... | 600/426 |
| 5,238,870 A | * | 8/1993 | Tanaka ........................ | 438/296 |
| 6,416,219 B1 | * | 7/2002 | Pflaum et al. ............... | 378/209 |
| 6,628,746 B2 | * | 9/2003 | Eppler et al. ................. | 378/21 |
| 6,662,036 B2 | * | 12/2003 | Cosman ....................... | 600/411 |
| 2001/0049475 A1 | * | 12/2001 | Bucholz et al. ............. | 600/411 |

* cited by examiner

Primary Examiner—Craig E. Church
Assistant Examiner—Thomas R Artman

(57) ABSTRACT

An x-ray laminography imaging system and a positioning system to be used therewith. The positioning system is configured to move the object in the X, Y and Z-directions (i.e., pitch and roll) to ensure that the object planes of the object that are being imaged are at least substantially parallel to the focal plane of the imaging system. The object is positioned so that object planes associated with the X, Y and Z-coordinates of points along the contour of the surface of the object are at least substantially parallel to the focal plane of the imaging system during imaging of the object plane. Because some objects, such as printed circuit boards, for example, are sometimes warped, by ensuring that the object plane being imaged is at least substantially parallel to the focal plane of the imaging system, precise laminographs are obtained. The preciseness of the laminographs ensures that the cross-sectional slices of the object are accurate, which improves the robustness of an inspection system that uses x-ray laminography to inspect objects.

30 Claims, 3 Drawing Sheets

X-RAY LAMINOGRAPHY SYSTEM HAVING A PITCH, ROLL AND Z-MOTION POSITIONING SYSTEM

TECHNICAL FIELD OF THE INVENTION

The present invention relates to x-ray imaging and, more particularly, to a positioning system for use in positioning an object when performing x-ray laminography.

BACKGROUND OF THE INVENTION

Laminography techniques are widely used to produce cross-sectional images of selected planes within objects. Conventional laminography requires coordinated motion of any two of three main components comprising a laminography system (i.e., a radiation source, an object being inspected, and a detector). The coordinated motion of the two components can be in any of a variety of patterns, including linear, circular, elliptical and random patterns. Regardless of the pattern of coordinated motion selected, the configuration of the source, object and detector should ensure that, during a cycle of the pattern of motion, any given point in the object plane (i.e., the plane of focus within the object) will always be projected onto the same point in the image plane (i.e., the plane of the detector), and that any point outside the object plane will be projected to a plurality of points in the image plane.

In laminography, it is important to keep the focal plane very thin. If the coordinated motion is as it should be, a sharp cross-sectional image of the plane within the object that is in focus will be formed on the detector. Cross-sections of the object that are not in the focal plane (i.e., background images) will be blurred on the detector. The result is a sharp image of the desired plane within the object. In a laminography system that has a field of view that is smaller than the object being inspected, it may be necessary to move the object around within the field of view (FOV) of the laminography system to obtain multiple laminographs which, when pieced together, cover the entire object. Movement of the object is frequently achieved by supporting the object on a mechanical handling system, such as an X, Y, Z positioning table, that can be moved in the X, Y and Z directions. The table is moved to bring the desired X, Y regions of the object into the field of view (FOV) of the laminography system. Once the X, Y region of the object to be imaged is within the FOV, the object is moved in the Z directions so that the planes within the object where the cross-sectional image is to be obtained are generally parallel to the focal plane of the laminography system. Once the desired planes within the object along the Z-axis have been imaged for a given X, Y region, the X, Y, Z positioning table moves the object so that the next X, Y region to be imaged is within the FOV of the laminography system. The desired planes within the object along the Z-axis are then imaged by moving the object to selected positions along the Z-axis. This process continues until all of the desired cross-sectional images, or slices, needed to inspect the object have been obtained.

While this method of moving the object in the X, Y and Z directions to perform laminography enables various areas and planes of the object to be imaged and analyzed, there are limitations associated with the speed and accuracy of existing mechanical positioning systems. These constraints effectively act to increase cycle time, thereby reducing the rates at which inspection can occur. Furthermore, with existing mechanical positioning systems, the mechanical motions produce vibrations that tend to reduce the system resolution and accuracy. In addition, the laminographs obtained by such systems may be imprecise.

Accordingly, a need exists for a laminography positioning system that improves the accuracy of the laminographs and that enables laminographic inspection to be performed with great precision and improved throughput.

SUMMARY OF THE INVENTION

The present invention provides an x-ray laminography imaging system and a positioning system to be used therewith. The positioning system is configured to move the object in the X, Y and Z-directions and to impart pitch and roll motions to the object. The object is selectively positioned so that object planes associated with points along the contour of the surface of the object are at least substantially parallel to the focal plane of the imaging system during imaging. Because some objects, such as printed circuit boards, for example, are sometimes warped, ensuring that the object plane being imaged is at least substantially parallel to the focal plane of the imaging system, enables precise laminographs to be obtained. The preciseness of the laminographs ensures that the cross-sectional slices of the object that are obtained are accurate, which is important for many reasons, including to improve the robustness of an inspection system that uses x-ray laminography to inspect objects.

The present invention also provides a method for performing x-ray laminography with an x-ray laminography imaging system. The method comprises the steps of projecting x-rays from an x-ray source onto an object to be imaged, detecting x-rays that pass through the object with an x-ray detector, and positioning system the object so that object planes associated with points on the contour of the surface of the object are at least substantially parallel to a focal plane of the imaging system when the object planes are imaged.

These and other features and advantages of the present invention will become apparent from the following description, drawings and claims.

DETAILED DESCRIPTION OF THE PREFERRED EMBODIMENTS

Existing laminography techniques assume that the object being imaged is parallel in all dimensions to the focal plane of the laminography system. Therefore, for any given X, Y region of the object being imaged, the object is only moved in the Z-directions (i.e., along the axis normal to the focal plane). The assumption that the object plane is parallel to the focal plane is not always true, which can result in the focal plane being at an oblique angle to the plane within the object being imaged. If the plane within the object being imaged (i.e., the object plane) is not parallel to the focal plane of the laminography system, the resulting laminographs will contain inaccuracies, which can cause difficulties. For example, if the x-ray laminography system is being used to inspect objects, inaccuracies in the laminographs will degrade the quality of the inspection process and can increase the amount of time required to inspect the object.

Some objects, such as printed circuit boards (PCBs), for example, are often warped or wavy. In such a case, for each X, Y region, the planes to be imaged within the object often will not be parallel to the focal plane of the laminography system, which results in imprecise laminographs. In accordance with the present invention, a pitch, roll and Z (P, R, Z) positioning system is provided that enables the object to be precisely positioned such that, for each X, Y region, the plane within the object being imaged is parallel to the focal plane of the laminography system. This ensures that the laminographs will be precise, and thus increases the robustness of the laminography inspection process.

Figure 1:
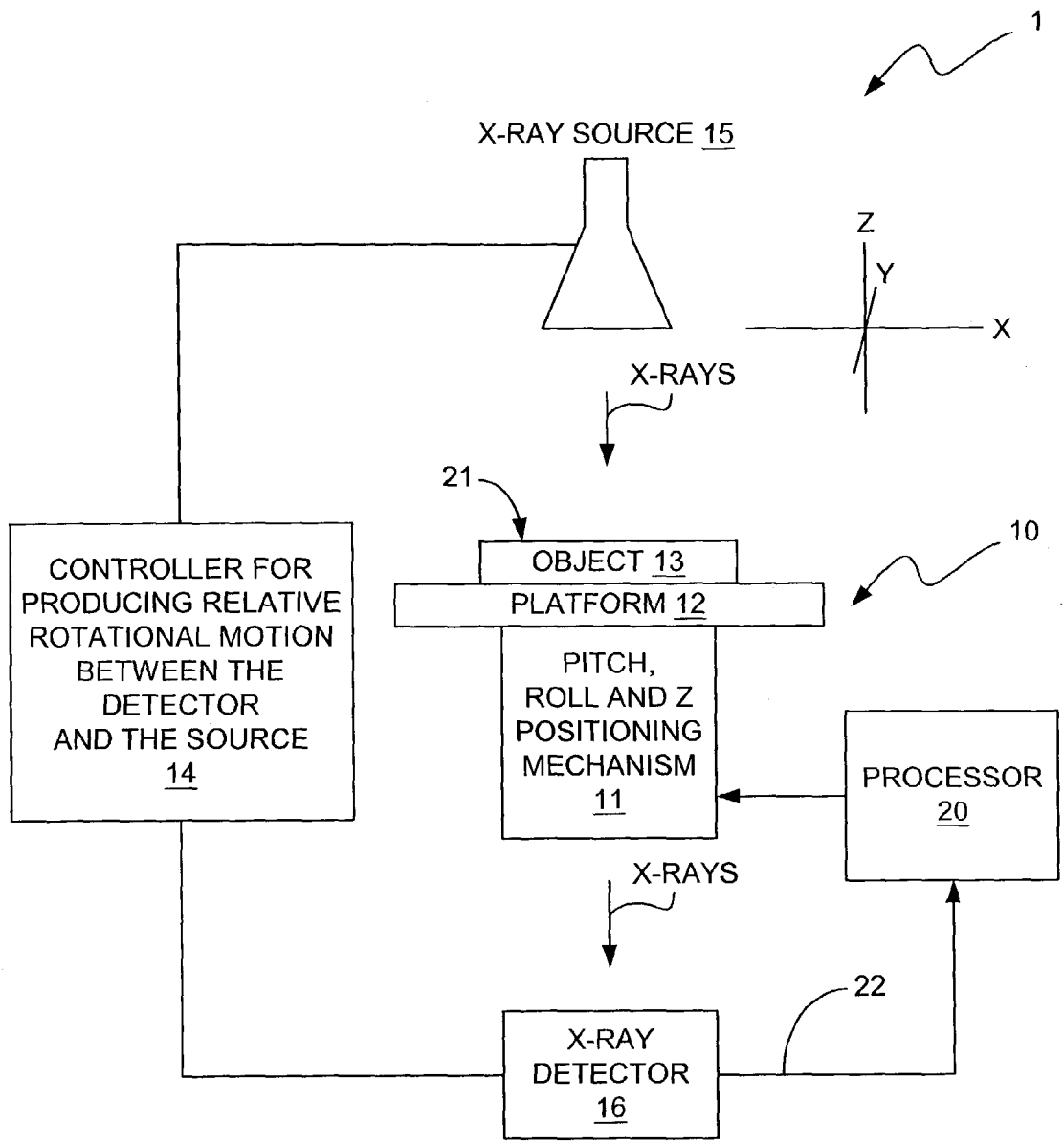
FIG. 1 is a schematic view of a laminography system in accordance with an embodiment of the present invention.

With reference to FIG. 1, in accordance with the present invention, the term pitch corresponds to rotational motion of the object about the Y-axis and the term roll corresponds to rotational motion of the object about the X-axis. By providing a positioning system that combines P, R, Z positioning of the object, the object can be positioned so that the plane within the object being imaged is always parallel to the focal plane of the laminography system.

FIG. 1 is a block diagram of a laminography system 1 that utilizes the P, R, Z positioning system 10 of the present invention. The P, R, Z positioning system comprises a P, R, Z positioning mechanism 11 and a platform 12. The object under inspection 13 is positioned on the platform 12. A controller 14 coordinates the relative motion of the X-ray source 15 and that of the x-ray detector 16 to ensure that any given point in the focal plane is projected onto the same spot on the detector 16 during a cycle of the motion pattern. The coordinated motion of the x-ray source 15 and the x-ray detector 16 can be in any of a variety of patterns, including linear, circular, elliptical and random patterns. Regardless of the pattern of coordinated motion selected, during a cycle of the pattern of motion, any given point in the object plane (i.e., the plane of focus within the object 13 along the Z-axis) will always be projected onto the same point in the image plane (i.e., the plane of the detector). Also, any point outside the object plane will be projected to a plurality of points in the image plane so that images of planes outside of the focus plane will be blurred, thereby increasing the sharpness of the image within the focal plane. The manner in which the P, R, Z positioning system operates is described in detail below with reference to FIGS. 3A and 3B.

Figure 2:
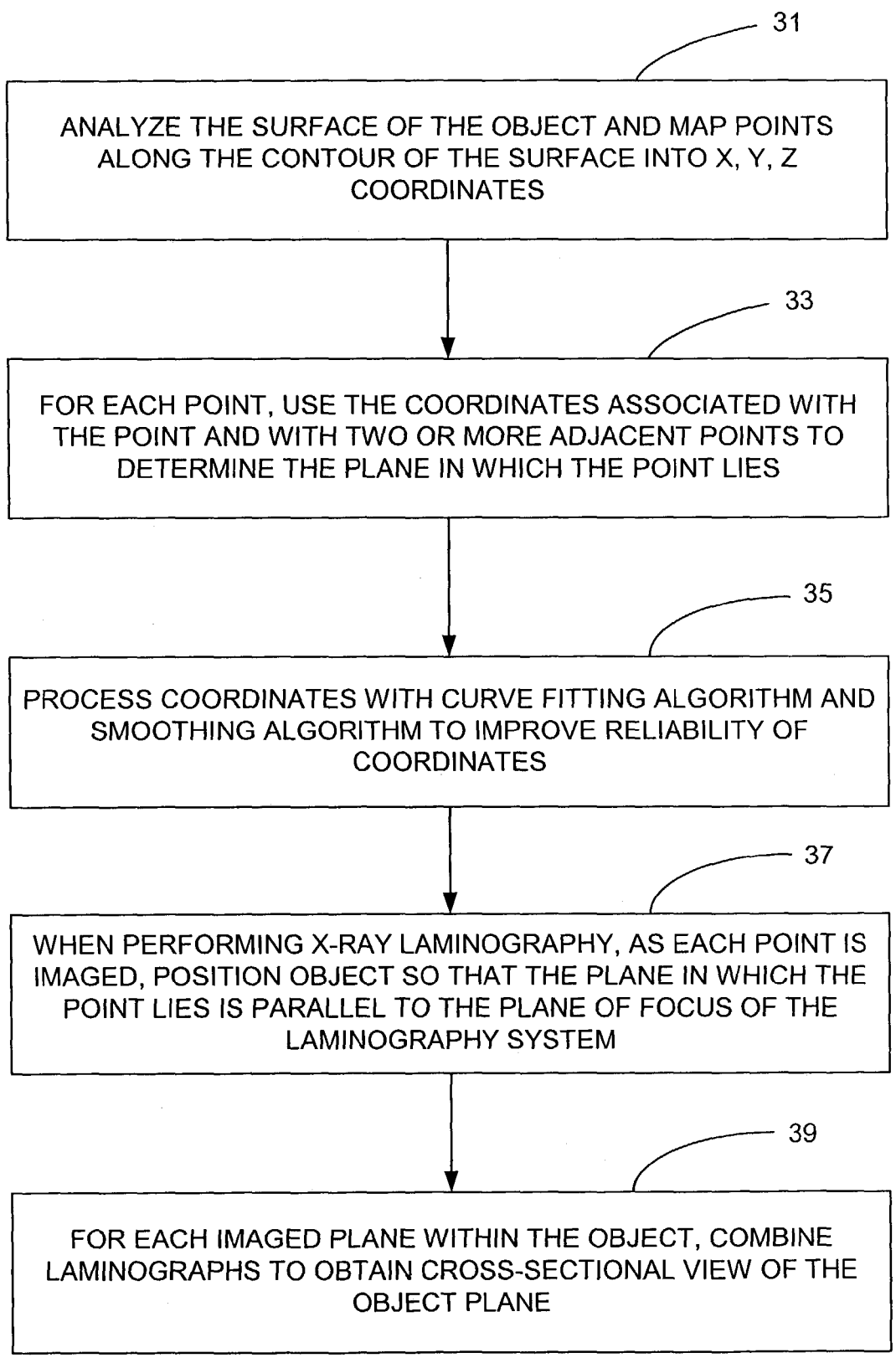
FIG. 2 illustrates a flow chart of the method of the present invention in accordance with an example embodiment.

The method of the present invention, in accordance with an example embodiment, will now be described with reference to the flow chart of FIG. 2. In accordance with this example embodiment, the processor 20 is provided with, or acquires, surface contour data. Known algorithms and systems exist that are used to analyze the surface of an object and map points on the surface into X, Y and Z coordinates. This step is represented by block 31. The algorithm for analyzing and mapping the data may be performed by the processor 20 or, alternatively, by other processor (not shown). In the latter case, the data would be generated and then provided to processor 20. In either case, the processor 20 uses the coordinate data to determine object planes at each of the points. This step is represented by block 33. Because the coordinates for three points define a plane, the coordinates of each object plane can be determined from the X, Y coordinates of three adjacent X, Y locations on the surface 21. The preciseness of the coordinates that define the planes improves as the number of points used to determine the planar coordinates increases. Therefore, the number of points on the surface of the object that are used for these calculation preferably is large, although the present invention is not limited with respect to the number of points used to perform the necessary calculations.

Once the object plane coordinates have been determined, a curve fitting algorithm preferably is used to process the object plane coordinate data in order to estimate (e.g., by interpolation) with high precision the coordinates of the object planes. This step is represented by block 35. Because the surface 21 of the object 13 is expected to be substantially flat, sharp transitions in the X, Y and Z coordinates should not occur. Therefore, a curve fitting algorithm that includes a smoothing function preferably is used for this purpose because such a smoothing function will operate to remove errors in the object plane coordinates and thereby ensure or improve the reliability of the coordinates.

Step 35, although preferred, is optional because, even without this further processing step, the positioning system of the present invention will inherently provide better results than existing positioning systems because the coordinate data obtained as a result of processing steps 31 and 33 is highly accurate and may be sufficiently precise for purposes of inspection. A variety of curve fitting algorithms are suitable for performing the processing represented by step 35. An example of a known algorithm that is suitable for this purpose is one that processes the data in accordance with a cubic spline function, which is a known curve fitting function.

When performing x-ray laminography 1, the processor 20 commands the P, R, Z positioning mechanism 11 to position the object 13 such that, for each selected point on the surface 21 of the object 13, the corresponding object plane is parallel to the focal plane of the laminography system 1. This step is represented by block 37. The resulting laminographs are delivered to the processor 20 (or to some other processor), as indicated by arrow 22 in FIG. 1.

Figure 3A:
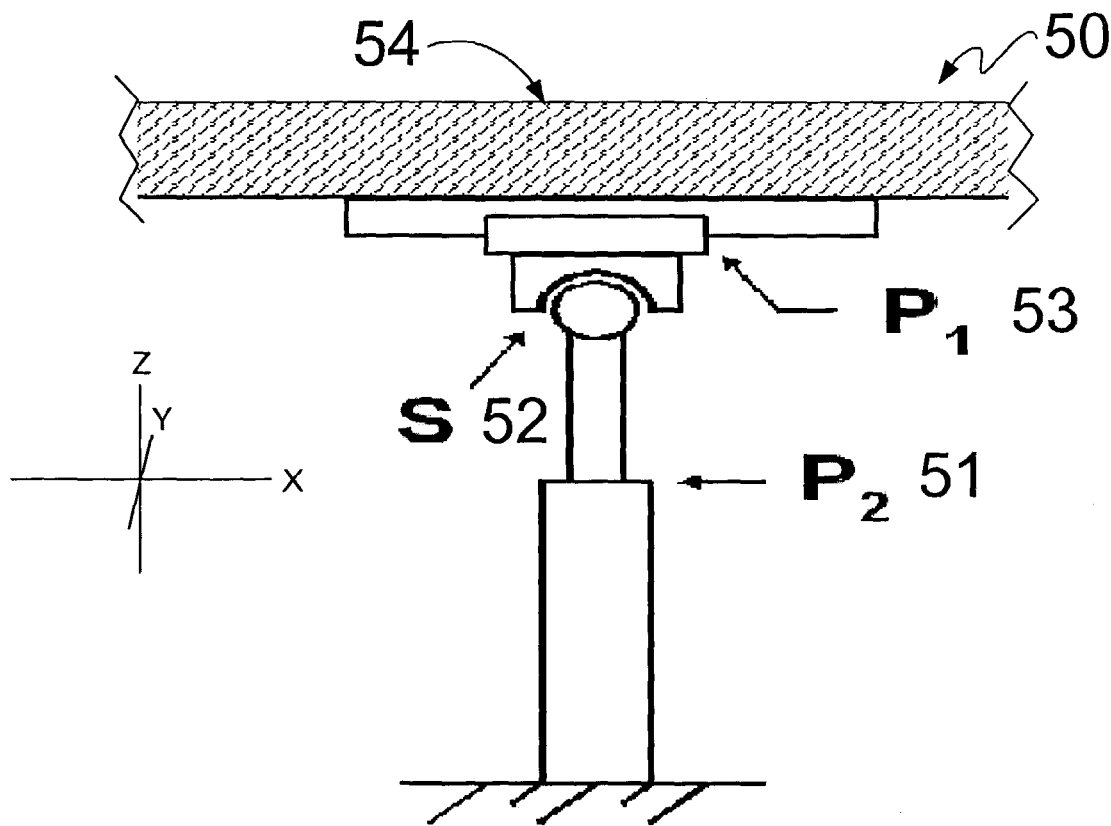
FIG. 3A is a side view of one of one of the prismatic-spherical-prismatic (PSP) joint configurations of the P, R, Z positioning system of the present invention in accordance with an example embodiment.
Figure 3B:
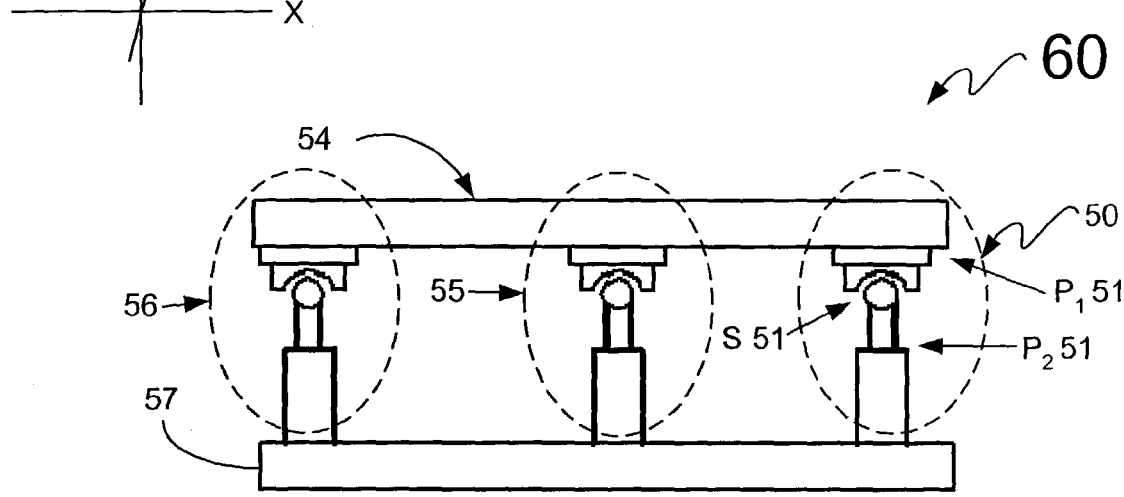
FIG. 3B is a side view of the entire P, R, Z positioning system in accordance with the embodiment, which preferably comprises three of the PSP joint configurations shown in FIG. 3A.

FIG. 3A is a side view of one of one of the prismatic-spherical-prismatic (PSP) joint configurations 50 of the P, R, Z positioning system of the present invention in accordance with an example embodiment. FIG. 3B is a side view of the entire positioning system 60, which preferably comprises three of the PSP joint configurations shown in FIG. 3A. The three PSP joint configurations 50, 55 and 56 preferably are joined in a three-PSP actuator assembly to complete the P, R, Z positioning system 60. With reference to FIG. 3A, the PSP joint configuration 50 comprises a joint $P_2$ 51, which may be, for example, a telescoping ballscrew actuator driven by an electric motor (not shown), an S joint 52, which may be, for example, a ball-and-socket joint, and a joint $P_1$ 53, which may comprise, for example, a linear bearing having one or more rolling elements.

The present invention is not limited to the configuration 50. For example, a universal or Cardan joint, flexure, or any other spherical joint may be used as the S joint 52. With respect to joint $P_1$ 43, rolling elements with simple sliders, flexure or any other prismatic guide may be used in place of the aforementioned ball-and socket joint. With respect to $P_2$ 41, any prismatic actuator can be used in place of the telescoping ballscrew actuator. Those skilled in the art will understand, in view of the present disclosure, the manner in which these and other variations can be made to the joint configurations S, $P_1$ and $P_2$ without deviating from the scope of the present invention.

As stated above, FIG. 3B illustrates a side view of three PSP joint configurations 50, 55 and 56 that are spaced apart in the X-coordinate directions and are joined to a moving object platform 54 and to a fixed base 57. The combination of the three PSP joint configurations 50, 55 and 56 results in a P, R, Z positioning system 50 with multiple degrees of freedom, which creates relative motion between the fixed base 57 and the moving platform 54. If all three actuators 51 ($P_2$ joints), 52 (S joints) and 52 ($P_1$ joints) move by the same amount and in the same direction, only translation of the platform 54 in the Z-direction will occur. By moving the three actuators 51, 55 and 56 by different amounts, various combinations of pitch rotation, roll rotation and Z translation of the platform 54 will result. This allows the platform 54 to be positioned in any arbitrary plane within the workspace of the laminography system so that the plane of the object being imaged is within the filed of depth of the system and is parallel to the focal plane of the system.

It should be noted that the positioning system 50 has a particular configuration that obviates the need to "stack" X and/or Y and/or Z translation components. The configuration shown in FIG. 3A is preferred because it is compact and very precise. It should be noted, however, that virtually an infinite number of configurations could be constructed that would enable the object to be translated in the X, Y and Z directions. For example, a positioning system that performs pitch, roll and Z motions could be configured by having a first platform that is translatable in the Z-directions, a second platform stacked on top of the first one that is translatable in the X-directions and a third platform stacked on top of the second platform that is translatable in the Y-directions. The object to be imaged would be placed on the uppermost platform. By coordinating the X, Y and Z translations of the respective platforms, pitch, roll and Z motion could be obtained. However, such as system would likely be less compact than the positioning system of the present invention, which could result in an increase in the dimensions of the positioning system. Also, such a positioning system would likely have additional moving parts that may decrease preciseness. Nevertheless, this and any other configuration that provides the necessary or desired motion are within the scope of the present invention.

One of the benefits of the positioning system 60 (FIG. 3B) is that it allows movement of an object being imaged towards the imaging optics to produce an in-focus image even when the depth of field of the optics is limited and would not otherwise (i.e., without the positioning system 50) produce and in-focus image. The positioning system 60 of the present invention is particularly well suited for use with x-ray laminography systems because laminography, by definition and design, provides a very limited depth of focus, which enables very thin slices within the object to be examined. This is particularly useful for x-ray laminographic inspection of PCBs because PCBs are often warped to a degree that is significant to laminography, and the P, R, Z positioning capability of the positioning system 60 ensures that the plane of the region of the object being inspected is parallel to the focal plane of the x-ray laminography system.

However, although the positioning system 60 of the present invention is particularly well suited for certain purposes or applications, its use is not limited to any particular applications. The positioning system of the present invention is suitable for use with any type of imaging system, and is especially useful in cases where it is important or necessary to move the object to meet depth-of-focus requirements and/or to ensure that the position of a planar area of the object being imaged is parallel to the focal plane of the imaging optics.

It should be noted that the present invention has been described only with reference to preferred embodiments for example purposes and in the interest of brevity, and that the present invention is not limited to these embodiments. Those skilled in the art will understand, in view of the present disclosure, the manner in which embodiments not disclosed herein can be developed by utilizing the principles and concepts of the present invention. These undisclosed embodiments are also within the scope of the present invention. Those skilled in the art will also understand that modifications can be made to the embodiments discussed herein and that all such modifications are within the scope of the present invention.

What is claimed is:

1. An x-ray laminography imaging system comprising:
   an x-ray source that projects x-rays onto an object being imaged;
   a detector that detects x-rays that pass through the object during a plurality of laminographic pattern scans;
   a positioning system configured to move the object in X, Y and Z-directions to cause each of a plurality of points at particular locations along a contour of a surface of the object to be positioned at a particular respective position when a particular respective object plane of the object is imaged, each respective position being defined by an X-coordinate, a Y-coordinate and a Z-coordinate, the X and Y-coordinates defining the positions in a first plane and the Z-coordinate defining the positions in a second plane that is non-parallel to the first plane, wherein the positioning system comprises at least three prismatic-spherical-prismatic (PSP) joint configurations, and wherein each joint configuration comprises at least a Z-direction actuator; and
   an electronic processor in communication with the positioning system, the processor being configured to execute an algorithm that generates electrical output data signals that control the positioning system, and wherein the output data signals cause the positioning system to move the object in selected X, Y and Z-directions to position each of said points at particular respective positions and impart motion to the object to cause the object plane associated with each respective point to be at least substantially coincident with or at least substantially parallel to a focal plane of the imaging system, the X and Y-directions being within the first plane, the Z-direction being within the second plane.

2. The x-ray laminography imaging system of claim 1, wherein the first and second planes are orthogonal to one another.

3. The x-ray laminography imaging system of claim 2, wherein the Z-direction is either toward the x-ray source or away from the x-ray source.

4. The x-ray laminography imaging system of claim 1, wherein the algorithm processes the X, Y and Z-coordinates corresponding to the positions of said points to determine the object plane associated with each of said points, and wherein the algorithm includes an object plane routine that utilizes the object planes associated with the points to generate the output data signals.

5. The x-ray laminography imaging system of claim 1, wherein the algorithm includes a curve-fitting routine, the curve-fitting routine processing the X, Y and Z-coordinates associated with each of the points to generate a curve, each point on the curve being defined by an X, Y and Z-coordinate, and wherein at least some of the points have X, Y and Z-coordinates that coincide with the curve and at least one of the points has X, Y and Z-coordinates that do not coincide with the curve, and wherein the curve-fitting routine generates the object planes by using the X, Y and Z-coordinates that define the curve.

6. The x-ray laminography imaging system of claim 1, wherein the algorithm includes an estimation routine, the estimation routine processing the X, Y and Z-coordinates associated with each point to generate estimated X, Y and Z-coordinates for each point, and wherein the estimation routine generates the object planes based on the estimated X, Y and Z-coordinates.

7. The x-ray laminography imaging system of claim 1, wherein the algorithm includes an interpolation routine, the interpolation routine processing the X, Y and Z-coordinates associated with each respective point to generate interpolated X, Y and Z-coordinates for each respective point, and wherein the algorithm generates the object planes based on the interpolated X, Y and Z-coordinates.

8. The x-ray laminography imaging system of claim 1, wherein the positioning system includes a base and an object platform, wherein each PSP joint configuration has a first end coupled to the base and a second end coupled to a bottom side of the platform, and wherein a point on the surface of the object is positioned at a selected position defined by a particular set of X, Y and Z-coordinates by moving one or more of the Z-direction actuators in the Z-direction by a selected distance.

9. The x-ray laminography imaging system of claim 8, wherein each PSP joint configuration comprises an S joint, a $P_1$ joint and a $P_2$ joint, the $P_2$ joint having a first terminating portion secured to the base and a second terminating portion coupled to a first terminating portion of the S joint, the S joint having a second terminating portion coupled to a first terminating portion of the $P_1$ joint, the $P_1$ joint having a second terminating portion coupled to the bottom of the object platform, and wherein the $P_2$ joint comprises a telescoping actuator driven by a motor, and wherein the motor receives input that causes the motor to drive an arm of the telescoping actuator forwards and rearwards in the Z-direction.

10. The x-ray laminography imaging system of claim 8, wherein each PSP joint configuration comprises an S joint, a $P_1$ joint and a $P_2$ joint, the $P_2$ joint having a first terminating portion secured to the base and a second terminating portion coupled to a first terminating portion of the S joint, the S joint having a second terminating portion coupled to a first terminating portion of the $P_1$ joint, the $P_1$ joint having a second terminating portion coupled to the object platform, and wherein the S joint is a ball-and-socket joint.

11. The x-ray laminography imaging system of claim 8, wherein each PSP joint configuration comprises an S joint, a $P_1$ joint and a $P_2$ joint, the $P_2$ joint having a first terminating portion secured to the base and a second terminating portion coupled to a first terminating portion of the S joint, the S joint having a second terminating portion coupled to a first terminating portion of the $P_1$ joint, the $P_1$ joint having a second terminating portion coupled to the object platform, and wherein the $P_1$ joint comprises a linear bearing.

12. An X-ray laminography imaging system comprising a positioning system for positioning an object by the imaging system to be imaged, the object being irradiated by a radiation source of the imaging system that projects radiation onto the object, and wherein at least some of the radiation projected onto the object impinges on a radiation detector of the imaging system, the imaging system comprising positioning system comprising:

a motor;

an actuator assembly, the actuator assembly being controlled by the motor, wherein the motor receives electrical signals that cause the motor to actuate the actuator assembly, the actuator assembly being configured to move the object in X, Y and Z directions to cause each of a plurality of points at particular locations along a contour of a surface of the object to be positioned at a particular respective position when a particular respective object plane of the object is imaged, the X-direction and the Y-direction being within a first plane, the Z-direction being within a second plane that is non-parallel to the first plane, and wherein the motion imparted to the object ensures that an object plane of the object being imaged is at least substantially parallel to a focal plane of the imaging system, wherein the actuator assembly comprises at least three prismatic-spherical-prismatic (PSP) joint configurations, and wherein each joint configuration comprises at least a Z-direction actuator; and an electronic processor in communication with the motor, the processor being configured to execute an algorithm that generates electrical signals that control the motor, and wherein the electrical signals cause the motor to actuate the actuator assembly to move the object in selected X, Y and Z-directions to position each of said points at particular respective positions.

13. The positioning system of claim 12, wherein the first and second planes are orthogonal to one another.

14. The positioning system of claim 13, wherein the Z-direction is either toward the x-ray source or away from the x-ray source.

15. The positioning system of claim 13, wherein the electrical signals received by the motor correspond to output data signals generated by a processor in communication with the motor, the processor being configured to execute an algorithm that generates the output data signals that cause the positioning system to move the object in the X, Y and Z-directions to particular positions defined by an X-coordinate, a Y-coordinate and a Z-coordinate such that the object plane to be imaged is at least substantially parallel to the focal plane of the imaging system.

16. The positioning system of claim 13, wherein the actuator assembly further comprises a base and an object platform, and wherein a point on the surface of the object is positioned at a selected position defined by a particular set of X, Y and Z-coordinates when the motor causes one or more of the Z-direction actuators to move in the Z-direction a selected distance.

17. The positioning system of claim 16, wherein each PSP joint configuration comprises an S joint, a $P_1$ joint and a $P_2$ joint, the $P_2$ joint having a first terminating portion secured to the base and a second terminating portion coupled to a first terminating portion of the S joint, the S joint having a second terminating portion coupled to a first terminating portion of the $P_1$ joint, the $P_1$ joint having a second terminating portion coupled to the bottom of the object platform, and wherein the $P_2$ joint comprises a telescoping actuator driven by a motor, and wherein the motor receives input that causes the motor to drive an arm of the telescoping actuator forwards and rearwards in the Z-direction.

18. The positioning system of claim 16, wherein each PSP joint configuration comprises an S joint, a $P_1$ joint and a $P_2$ joint, the $P_2$ joint having a first terminating portion secured to the base and a second terminating portion coupled to a first terminating portion of the S joint, the S joint having a second terminating portion coupled to a first terminating portion of the $P_1$ joint, the $P_1$ joint having a second terminating portion coupled to the bottom of the object platform, and wherein the S joint is a ball-and-socket joint.

19. The positioning system of claim 16, wherein each PSP joint configuration comprises an S joint, a $P_1$ joint and a $P_2$ joint the $P_2$ joint, having a first terminating portion secured to the base and a second terminating portion coupled to a first terminating portion of the S joint, the S joint having a second terminating portion coupled to a first terminating portion of the $P_1$ joint, the $P_1$ joint having a second terminating portion coupled to the bottom of the object platform, and wherein the $P_1$ joint comprises a linear bearing.

20. A method for performing x-ray laminography with an x-ray laminography imaging system, the method comprising the steps of:
projecting x-rays from an x-ray source onto an object to be imaged;
detecting x-rays that pass through the object with an x-ray detector during a plurality of laminographic pattern scans;
utilizing a positioning system to impart motion to the object in an X-direction, a Y-direction and a Z-direction to cause object planes associated with points on the contour of the surface of the object to be positioned at selected positions that are parallel to a focal plane of the imaging system when the object planes are imaged, each of the selected positions being defined by an X-coordinate, a Y-coordinate and a Z-coordinate, the X and Y-coordinates defining positions in a first plane and the Z-coordinate defining positions in a second plane that is non-parallel to the first plane, the X-direction and the Y-direction being within the first plane, the Z-direction being within the second plane that is non-parallel to the first plane, wherein the positioning system comprises an actuator assembly, and the actuator assembly comprises a motor, wherein the positioning system comprises at least three prismatic-spherical-prismatic (PSP) joint configurations, and wherein each joint configuration comprises at least a Z-direction actuator;
generating electrical output data signals with an electronic processor, the processor executing an algorithm that generates the output data signals; and
delivering the output data signals to the motor so that the motor causes the actuator assembly to move the object in the X, Y and Z-directions to position the object at one of the selected positions such that an object plane to be imaged is at least substantially parallel to the focal plane of the imaging system.

21. The method of claim 20, wherein the first and second planes are orthogonal to one another.

22. The method of claim 21, wherein the Z-direction is either toward the x-ray source or away from the x-ray source.

23. The method of claim 20, wherein the processor is configured to execute an algorithm that generates the output data signals, and wherein the algorithm includes a focal plane routine that processes the X, Y and Z-coordinates associated with the points to determine the object planes associated with the points, the generated by the processor and delivered to the motor causing the positioning system to position the object such that the object plane being imaged is at least substantially parallel to a focal plane of the imaging system.

24. The method of claim 20, wherein the algorithm includes a curve-fitting routine, the curve-fitting routine processing the X, Y and Z-coordinates associated with each point to generate a curve, each point on the curve being defined by an X, Y and Z-coordinate, and wherein at least some of the points have X, Y and Z-coordinates that coincide with the curve and at least one of the points has X, Y and Z-coordinates that do not coincide with the curve, and wherein the routine generates the object planes based on the X, Y and Z-coordinates that define the curve.

25. The method of claim 20, wherein the algorithm includes an estimation routine, the estimation routine processing the X, Y and Z-coordinates associated with each respective point to generate estimated X, Y and Z-coordinates for each respective point, and wherein the algorithm generates the object planes based on the estimated X, Y and Z-coordinates.

26. The method of claim 20, wherein the algorithm includes an interpolation routine, the interpolation routine processing the X, Y and Z-coordinates associated with each respective point to generate interpolated X, Y and Z-coordinates for each respective point, and wherein the algorithm generates the object planes based on the interpolated X, Y and Z-coordinates.

27. The method of claim 20, wherein the positioning system includes a base and an object platform, wherein each PSP joint configuration has a first end coupled to the base and a second end coupled to a bottom a bottom side of the platform, and wherein a point on the surface of the object is positioned at a selected position defined by a particular set of X, Y and Z-coordinates by moving one or more of the Z-direction actuators in the Z-direction by a selected distance.

28. The method of claim 27, wherein each PSP joint configuration comprises an S joint, a $P_1$ joint and a $P_2$ joint, the $P_2$ joint having a first terminating portion secured to the base and a second terminating portion coupled to a first terminating portion of the S joint, the S joint having a second terminating portion coupled to a first terminating portion of the $P_1$ joint, the $P_1$ joint having a second terminating portion coupled to the bottom of the object platform, and wherein the $P_2$ joint comprises a telescoping actuator driven by a motor, and wherein the motor receives input that causes the motor to drive an arm of the telescoping actuator forwards and rearwards in the Z-direction.

29. The method of claim 27, wherein each PSP joint configuration comprises an S joint, a $P_1$ joint and a $P_2$ joint, the $P_2$ joint having a first terminating portion secured to the base and a second terminating portion coupled to a first terminating portion of the S joint, the S joint having a second terminating portion coupled to a first terminating portion of the $P_1$ joint, the $P_1$ joint having a second terminating portion coupled to the bottom of the object platform, and wherein the S joint is a ball-and-socket joint.

30. The method of claim 27, wherein each PSP joint configuration comprises an S joint, a $P_1$ joint and a $P_2$ joint, the $P_2$ joint having a first terminating portion secured to the base and a second terminating portion coupled to a first terminating portion of the S joint, the S joint having a second terminating portion coupled to a first terminating portion of the $P_1$ joint, the $P_1$ joint having a second terminating portion coupled to the bottom of the object platform, and wherein the $P_1$ joint comprises a linear bearing.

* * * * *

UNITED STATES PATENT AND TRADEMARK OFFICE
CERTIFICATE OF CORRECTION

| | | |
|---|---|---|
| PATENT NO. | : 6,977,985 B2 | Page 1 of 1 |
| APPLICATION NO. | : 10/321255 | |
| DATED | : December 20, 2005 | |
| INVENTOR(S) | : Bohn et al. | |

It is certified that error appears in the above-identified patent and that said Letters Patent is hereby corrected as shown below:

In column 8, lines 1-2, in Claim 12, delete "comprising" and insert -- comprising: --, therefor.

In column 8, line 2, in Claim 12, insert -- a -- before "positioning".

In column 9, line 8, in Claim 19, delete "joint" and insert -- joint, --, therefor.

In column 9, line 8, in Claim 19, after "P2 joint" delete ",".

Signed and Sealed this

Twenty-first Day of November, 2006

JON W. DUDAS
*Director of the United States Patent and Trademark Office*